United States Patent [19]

Shirafuji et al.

[11] Patent Number: 5,310,741
[45] Date of Patent: May 10, 1994

[54] **TAN-1251 COMPOUNDS AND THEIR PRODUCTION FROM *PENICILLIUM THOMII***

[75] Inventors: Hideo Shirafuji, Nagaokakyo; Shigetoshi Tsubotani, Kawanishi; Takenori Ishimaru, Toyonaka; Setsuo Harada, Kawanishi, all of Japan

[73] Assignee: Takeda Chemical Industries, Ltd., Osaka, Japan

[21] Appl. No.: 674,342

[22] PCT Filed: Mar. 5, 1991

[86] PCT No.: PCT/JP91/00295
§ 371 Date: Apr. 22, 1991
§ 102(e) Date: Apr. 22, 1991

[87] PCT Pub. No.: WO91/13887
PCT Pub. Date: Sep. 19, 1991

[30] Foreign Application Priority Data

Mar. 6, 1990 [JP] Japan .................. 2-55749
Mar. 1, 1991 [JP] Japan .................. 3-036107
Mar. 4, 1991 [JP] Japan .................. 3-037268

[51] Int. Cl.[5] .............. A01N 43/58; A61K 31/495; C07D 237/00; C12P 17/12
[52] U.S. Cl. .................. 514/249; 514/247; 514/248; 435/119; 435/122; 435/254.5; 435/933; 544/230; 544/231
[58] Field of Search ............... 544/230, 231; 435/254, 435/933, 119, 122; 424/93 Q; 514/248, 247, 249

[56] References Cited

FOREIGN PATENT DOCUMENTS

134648A2 5/1992 Japan .

*Primary Examiner*—Douglas W. Robinson
*Assistant Examiner*—Jeffrey J. Sevigny
*Attorney, Agent, or Firm*—Wenderoth, Lind & Ponack

[57] ABSTRACT

A compound of the formula

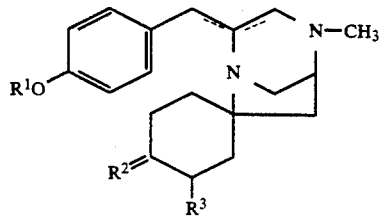

wherein $R^1$ is hydrogen or a hydrocarbon residue which may be substituted; $R^2$ is oxo or hydrogen plus hydroxy which may be acylated; $R^3$ is hydrogen or hydroxy which may be acylated; at least one of the dotted lines represents a single bond, or a salt thereof, produced from *Penicillum thomii* has potent RA-89 muscarinic receptor blocking activity and is of value as therapeutic agent for parkinsonism, ulcer, etc. or as mydriatics.

12 Claims, 5 Drawing Sheets

TAN-1251 COMPOUNDS AND THEIR PRODUCTION FROM *PENICILLIUM THOMII*

FIELD OF THE INVENTION

The present invention relates to a novel compound TAN-1251 (hereinafter sometimes referred to briefly as TAN-1251 which, unless otherwise indicated, means a series of TAN-1251 compounds) which is a muscarinic receptor blocking compound of value as a mydriatic or as an antispasmodic/antiulcer agent.

BACKGROUND OF THE INVENTION

The parasympathetic nerve inervates a diversity of peripheral tissues to manifest multi-facted activity. The receptors of acetylcholine, which is its neurotransmitter, are roughly classified into muscarinic receptors sensitive to muscarine which is an alkaloid of *Amanita muscaria* and nicotinic receptors sensitive to nicotine which is an alkaloid occurring in *Nicotiana tabacum*. Atropine and scopolamine, which are the alkaloids of the belladonna plants, have been utilized for centuries as nonspecific antimuscarinic drugs and are in use even today as mydriatics or antispasmodics [Goodman and Gilman's the Pharmacological Basis of Therapeutics, 7th ed., 130 (1985)].

It is known that muscarinic receptors can be classified into subtypes, i.e. M1 which has a high affinity for pirenzepine which is an antispasmodic/antiulcer agent and M2 which is low in that affinity [Nature 283, 90 (1980)]. Furthermore, a further ramification of muscarine M2 receptors according to their affinity for AF-DX 116 has been proposed [Life Sciences 38, 1653 (1986) and Clinical and Experimental Pharmacology and Physiology 16, 523 (1989)], and much research is in progress on methoctoramine and other compounds having subtype specificity [Trends in Pharmacological Science 9, 216 (1988)].

On the other hand, muscarinic receptor genes have been cloned by genetic engineering techniques [FEBS Letters, 235, 257 (1986)] and so far at least 5 kinds of genes have been reported to exist in man. While the pharmacologic correspondence of them to receptors remains yet to be elucidated, it will not be long before it is clarified [Trends in Pharmacological Science 12, 148 (1989)]. It is expected that muscarinic blockers having novel pharmacologic activity will be developed in this milieu.

Under the circumstances, search for muscarinic receptor blocking substances in microbial metabolites is also in progress. In fact, Eulissin, Argvalin, IJ2702-I & 2702-II and PF6766 [Journal of The Agricultural Chemical Society of Japan, 62, 338 (1988)] have already been reported but none of them have sufficiently potent activity.

In the above-mentioned situation, the inventors of the present invention explored microbial metabolites for novel compounds which would exhibit potent muscarinic blocking activity and discovered a TAN-1251 series of compounds having strong antimuscarinic activity. TAN-1251 is comprised of 4 species which the inventors designated TAN-1251A, B, C and D. Subsequent research revealed that these compounds have the following structures:

TAN-1251A:

TAN-1251B:

TAN-1251C:

TAN-1251D:

The inventors of the present invention further conducted degradation and derivatizing experiments using TAN-1251A, B, C and D as starting compounds and examined the biological activity of the degradation products and derivatives. As a result, they found that the following compounds were promising candidates for antispasmodic/antiulcer agents. The finding prompted further study which has resulted in the present invention.

SUMMARY OF THE INVENTION

Thus, the present invention is directed to:
1. A compound of the formula wherein $R^1$ is hydrogen or a hydrocarbon residue which may be substituted; $R^2$ is oxo or hydrogen and a hydroxy which may be acylated; $R^3$ is hydrogen or hydroxy which may be acylated; at least one of the dotted lines represents a single bond, or a salt thereof.

2. A method of producing a compound of the formula wherein $R^{3'}$ is hydrogen or hydroxy; at least one of the dotted lines represents a single bond; provided that where $R^{3'}$ is hydroxy, the dotted line on the right-hand side represents a single bond and the one on the left-hand side represents a double bond, or a salt thereof, characterized by culturing a strain of microorganism belonging to the genus Penicillium and capable of producing at least one compound having the above general formula in a culture medium and harvesting the same from the resulting culture broth.

3. A method of producing a compound of the general formula wherein the respective symbols have the meanings defined below, or a salt thereof characterized in that a compound of the general formula wherein $R^{1'}$ is 3-methyl-2-butenyl or 3-methylbutyl; $R^2$ is oxo or hydrogen and hydroxy which may be acylated; $R^3$ is hydrogen or hydroxy which may be acylated; at least one of the dotted lines represents a single bond, or a salt thereof is treated with an acid.

4. A method of producing a compound of the general formula wherein the respective symbols have the meanings defined below, or a salt thereof, characterized by reducing a compound of the general formula wherein $R^1$ is hydrogen or a hydrocarbon residue which may be substituted; $R^3$ is hydrogen or hydroxy which may be acylated; at least one of the dotted lines represents a single bond, or a salt thereof.

5. A method of producing a compound of the general formula wherein the respective symbols have the meanings defined below characterized in that a compound of the general formula wherein $R^2$ is oxy or hydrogen and hydroxy which may be acylated; $R^3$ is hydrogen or hydroxy which may be acylated, or a salt thereof is catalytically reduced.

6. A method of producing a compound of the general formula wherein the respective symbols have the meanings defined hereinbefore or below, characterized in that a compound of general formula (I) is reacted with a compound of the general formula

$R^4$-X        (IX)

wherein $R^4$ is alkyl; X is halogen.

7. A method of producing a compound of the general formula (XII)

wherein the respective symbols have the meanings defined below, or a salt thereof, characterized in that a culture broth, as it is or as processed, of a microorganism of the genus Penicillium is allowed to contact a compound of the general formula (XI)

wherein $R^1$ is a hydrogen or a hydrocarbon residue which may be substituted; $R^2$ is oxo or a hydrogen and a hydroxy which may be acylated; at least one of the dotted lines represents a single bond, or a salt thereof.

8. An antispasmodic/antiulcer composition containing a compound of the formula (I) or a pharmacologically acceptable salt thereof.

9. An antispasmodic composition containing a compound of the formula (I) or a pharmacologically acceptable salt thereof.

10. An antiulcer composition containing a compound of the formula (I) or a pharmacologically acceptable salt thereof.

BRIEF DESCRIPTION OF THE DRAWINGS

FIG. 6 shows a $^{13}C$ NMR spectrum of TAN-1251B.

DETAILED DESCRIPTION OF THE PREFERRED EMBODIMENT

Referring to the hydrocarbon residue which may be substituted, i.e. $R^1$ in the above general formulas, preferred examples of the hydrocarbon group are straight-chain or branched alkyl, alkenyl and alkynyl groups of 1 to 6 carbon atoms. Thus, the alkyl group includes, inter alia, methyl, ethyl, propyl, isopropyl, butyl, 1-methylpropyl, 2-methylpropyl, t-butyl, pentyl, 2-methylbutyl, 3-methylbutyl, hexyl, 4-methylpentyl, etc. The alkenyl group includes, inter alia, 2-propyl, 2-butenyl, 3-butenyl, 2-methyl-2-propenyl, 2-pentenyl, 3-pentenyl, 4-pentenyl, 2-methyl-2-butenyl, 3-methyl-2-butenyl, 2-hexenyl, 3-hexenyl, 4-hexenyl, 5-hexenyl, 3-methyl-2-pentenyl, 4-methyl-3-pentenyl, etc. The alkynyl group includes, inter alia, 2-propyl, 1-methyl-2-propynyl, 2-butynyl, 3-butynyl, 1-methyl-2-butynyl, 2-pentynyl, 3-pentynyl, 4-pentynyl, 2-methyl-3-pentynyl, 2-hexynyl and so on. The substituent or substituents thereon include, inter alia, $C_{3-6}$ cycloalkyl (e.g. cyclopropyl, cyclobutyl, cyclopentyl, cyclohexyl, etc.), phenyl which may be substituted (e.g. phenyl, o-hydroxyphenyl, m-hydroxyphenyl, p-hydroxyphenyl, etc.), hydroxy, mercapto, $C_{1-3}$ alkylthio (e.g. methylthio, ethylthio, propylthio, etc.), carboxy, guanidino, amino, imidazolyl and so on.

As examples of such substituted hydrocarbon groups, there may be mentioned cyclohexylmethyl, benzyl, p-hydroxybenzyl, hydroxymethyl, mercaptomethyl, 1-hydroxyethyl, 2-methylthioethyl, carboxymethyl, 2-carboxyethyl, 3-quanidino-propyl, 4-aminobutyl, 4-imidazolylmethyl, etc.

Referring to the hydroxy which may be acylated, as represented by $R^2$ and $R^3$ in the above general formulas, the acyl group includes aromatic acyl groups such as phthaloyl, p-nitrobenzoyl, p-tert-butylbenzoyl, p-tert-butylbenzensulfonyl, benzensulfonyl, toluenesulfonyl, etc. and aliphatic acyl groups such as formyl, actyl, propionyl, monochloroacetyl, dichloroacetyl, trichloroacetyl, methanesulfonyl, ethanesulfonyl, trifluoroacetyl, malonyl, succinyl and so on.

The salts of the above-mentioned compounds include, inter alia, salts of the conventional kinds, such as the corresponding hydrochlorides, sulfates, phosphates, etc., and the quaternary salts with the nitrogen atom in 4-position, and these salts can be produced by the processes described hereinafter.

The microorganism to be employed for the production of TAN-1251A, B, C and/or D in accordance with the present invention may be any microorganism belonging to the genus Penicillium and capable of producing TAN-1251A, B, C and/or D. As an example of such microorganism, there may be mentioned *Penicillium thomii* RA-89 which the inventors isolated from the soil in Miyagi Prefecture. The micrological characteristics of this strain are as follows.

(a) Morphological characteristics

The RA-89 strain shows good growth on malt extract agar, potato glucose agar and other media, producing abundant conidia. The hyphae are transparent and septate, and conidiophores are adnate from the substrate and aerial mycellia. The conidiophores show little branching but occur singly and are more than 200 μm long, each having a rough surface with spikes and a swollen end. Detected at the end of the conidiophore are more than 10 phialides in a brush-like formation (penicilli), with tens of conidia arranged in brush-like chains. The conidia are oblong or oval, measuring 3.5~4.0×2.3~2.8 μm, and have a rough surface. Moreover, the RA-89 strain forms a multiplicity of sclerotia. These sclerotia are amorphous, although primarily oval or spherical, measure about 300 μm, and although white in an early stage of formation, turn brown with a tinge or orange on aging. Further observation was continued but the sclerotia did not ripen to form ascospores.

(b) Cultural characteristics

The strain was cultured on various media at 28° C. for 2 weeks. The results are shown below in Tables 1 and 2.

TABLE 1

Cultural characteristics of *P. thomii* RA-89

| Agar medium | Growth on medium | Reverse color of colony | Conidium Formation | Conidium Color | Sclerotium | Soluble pigment | Diameter of colony |
| --- | --- | --- | --- | --- | --- | --- | --- |
| Malt extract | Good, not diffuse, velvety, white | Center: red yellow Margin: Light yellow | Good | Gray green | Abundant | None | 58 (mm) |
| Potato glucose | Good, not diffuse, velvety, white | Light scarlet | Good | Gray green | Abundant | None | 55 |
| Czapek | Good, not diffuse, velvety, white | Light brown to light purple | Good | Gray white Annular green | Abundant | None | 50 |
| Sabouraud | Good, not diffuse, felt-like, white | Yellow | Poor | White | Occasionally found | None | 40 |

TABLE 2

Cultural characteristics of *P. thomii* RA-89

| Agar medium | Growth on medium | Reverse color of colony | Conidium Formation | Conidium Color | Sclerotium | Soluble pigment | Diameter of colony |
| --- | --- | --- | --- | --- | --- | --- | --- |
| Oatmeal | Moderate, not diffuse, velvety, white | White to light yellow | Good | Gray green | Moderate | None | 55 (mm) |
| Synthetic mucor | Good, not diffuse, felt-like, white | White to light yellow | Poor | White | Moderate | None | 45 |
| Yeast extract soluble starch | Moderate, not diffuse, velvety, white | White | Good | Gray green | Abundant | None | 55 |

(c) Physiological Characteristics

The conditions for growth of *P. thomii* RA-89 were investigated using a potato glucose agar medium. The optimal temperature and pH for growth were 25°~30° C. and pH 4~5. The temperature range for growth was 5°-32.5° C. and the pH range for growth was pH 3~pH 7.

Comparing the above data, particularly morphological findings, with the descriptions in A Manual of the Penicillia (1949, The Williams and Wilkins Company) and The genus Penicillium and its Teleomorphic States Eupenicillium and Talaromyces (1979, Academic Press), the inventors identified the RA-89 strain as *Penicillium thomii* Maire.

This strain *Penicillium thomii* RA-89 has been deposited with the Institute for Fermentation, Osaka (IFO) as of Dec. 25, 1989 under the deposit number of IFO-32288 and with Fermentation Research Institute of the Agency for Industrial Research and Technology, the Ministry of International Trade and Industry as of Feb. 7, 1990 under the deposit number of FERM BP-2753.

The TAN-1251A, B, C and/or D-producing strains of microorganisms belonging to the genus Penicillium, like other fungi in general, can be caused to mutate by means of ultraviolet light, X-rays, and other radiations, by monospore isolation, or with various chemical mutagens, etc., and even the mutants so obtained and any spontaneous mutants can all be exploited for purposes of the present invention insofar as they cannot be substantially classified as strains of other species in view of the above taxonomical characteristics and as long as they retain the property to produce said particular compound or compounds.

The media for culture of such producer strains may be fluid or solid, only provided that they contain nutrients which the strains require and can utilize. However, fluid media are preferred for mass culture. The media should contain sources of carbon and nitrogen which the particular strains used may digest and assimilate, minerals and trace nutrients in appropriate amounts. The useful carbon source includes, inter alia, glucose, lactose, sucrose, maltose, dextrin, starch, glycerin, mannitol, sorbitol, oils and fats (e.g. soybean oil, lard oil, chicken oil, etc.) n-paraffin and so on. The nitrogen source includes, inter alia, meat extract, yeast extract, dried yeast, soybean flour, corn steep liquor, peptone, cottonseed flour, spent molasses, urea, ammonium salts (e.g. ammonium sulfate, ammonium chloride, ammonium nitrate, ammonium acetate, etc.) and so on. In addition, salts containing sodium, potassium, calcium, magnesium, etc., salts of metals such as iron, manganese, zinc, cobalt, nickel, etc., salts of phosphoric acid, boric acid, etc. and salts of organic acids such as acetic acid, propionic acid, etc. are incorporated in appropriate amounts. The medium may further contain amino acids (e.g. glutamic acid, aspartic acid, alanine, lysine, methionine, proline, etc.), peptides (e.g. dipeptides, tripeptides, etc.), vitamins (e.g. $B_1$, $B_2$, nicotinic acid, $B_{12}$, C, etc.) and nucleic acids (e.g. purine, pyrimidine and their derivatives). Of course, an inorganic or organic acid or base or a buffer for pH adjustment and an oil or fat or a surfactant as an antifoam can also be incorporated in suitable amounts. In fluid culture, the pH of the medium is preferably controlled near neutral, particularly pH 5.5~7. The incubation temperature and time are preferably about 20°~30° C. and about 48~168 hours.

The TAN-1251A, B, C and/or D which is produced with the progress of culture can be assayed by the radio receptor assay using a membrane fraction of the rat cerebral cortex as a crude receptor and $^3$H-QNB[L-[N-methyl-$^3$H]-quinuclidinyl benzilate methyl chloride (Amersham, U.K.) as a radioligand. Generally speaking, the production of TAN-1251A, B, C and/or D reaches a maximum in 4 to 5 days of culture.

TAN-1251, in general, being a basic and liposoluble substance, the product TAN-1251A, B, C and/or D can be harvested from the culture broth by utilizing these properties. Thus, since the respective component of TAN-1251 are accumulated in the filtrate of the broth, these compounds can be recovered by adjusting the filtrate to pH 7~11, preferably pH 8~10 and extracting them with a water-immiscible organic solvent such as dichloromethane, ethyl acetate, methyl isobutyl ketone or isobutyl alcohol. On the other hand, if the filtrate is adjusted to pH 1.5~6, preferably pH 2~4, and said organic solvent is added thereto, the active substance or substances will be brought into the aqueous layer. By taking advantage of this principle, one may advantageously recover the active substances by solvent redistribution or chromatography using an adsorbent resin such as Amberlite XAD-II (Rohm and Haas Co., U.S.A.), Diaion HP-20 (Mitsubishi Kasei, Japan) or Diaion SP-207 (Mitsubishi Kasei, Japan). For elution of the activity from a column packed with such an adsorbent resin, water or a hydrous solvent such as aqueous methanol, aqueous acetone, etc. can be employed. By concentrating the resulting extract or eluate under reduced pressure, a crude product containing the various species of TAN-1251 is obtained.

For isolation of the respective components of TAN-1251 by purification of the above crude product, a variety of chromatographic techniques can be employed with advantage. The stationary phase or packing material may be silica gel, cellulose, Sephadex LH-20 (Pharmacia, Sweden) or the like, and such packing material can be used in the manner of conventional column chromatography. Elution of the activity from such a column can be carried out using an appropriate organic solvent such as hexane, toluene, chloroform, ethyl acetate, dichloroethane, acetone, methanol, etc., as used independently or as a suitable mixture. The eluate thus obtained is concentrated to dryness or freeze-dried, or the concentrate is dissolved in an appropriate solvent such as diethyl ether, ethyl acetate or methanol or a mixture of such solvents and allowed to stand in the cold, whereby the respective species of TAN-1251 can be isolated as powders or crystals.

If the powder obtained in the above manner is not sufficiently high in purity, the technique of high performance liquid chromatography (HPLC) can be advantageously employed for further purification. The stationary phase for HPLC may for example be a reverse-phase column octadecylsilane such as YMC Gel (YMC, Japan) or TSK Gel (Toso, Japan), while the mobile phase may for example be a mixture of acetonitrile or methanol with either an acid, an inorganic salt-containing solution or a buffer solution.

Since each species of TAN-1251 is a basic substance, it can be treated with a suitable mineral acid to give the corresponding salt. The salt can be prepared in the per se known manner. Examples of such salt are the hydrochloride, sulfate, phosphate and so on.

Below presented as the physicochemical properties of the respective species of TAN-1251 prepared in the Examples given hereinafter.

Figure 1:
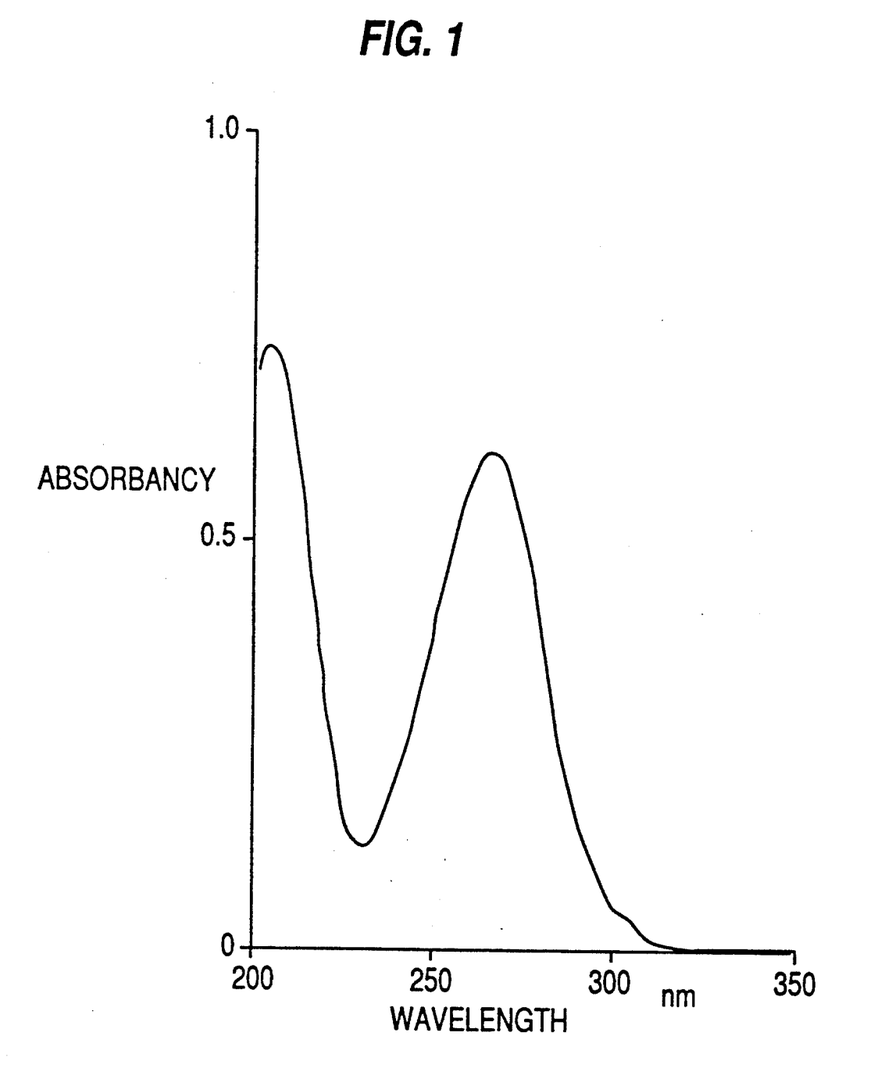
FIG. 1 shows an UV spectrum of TAN-1251A.
Figure 2:
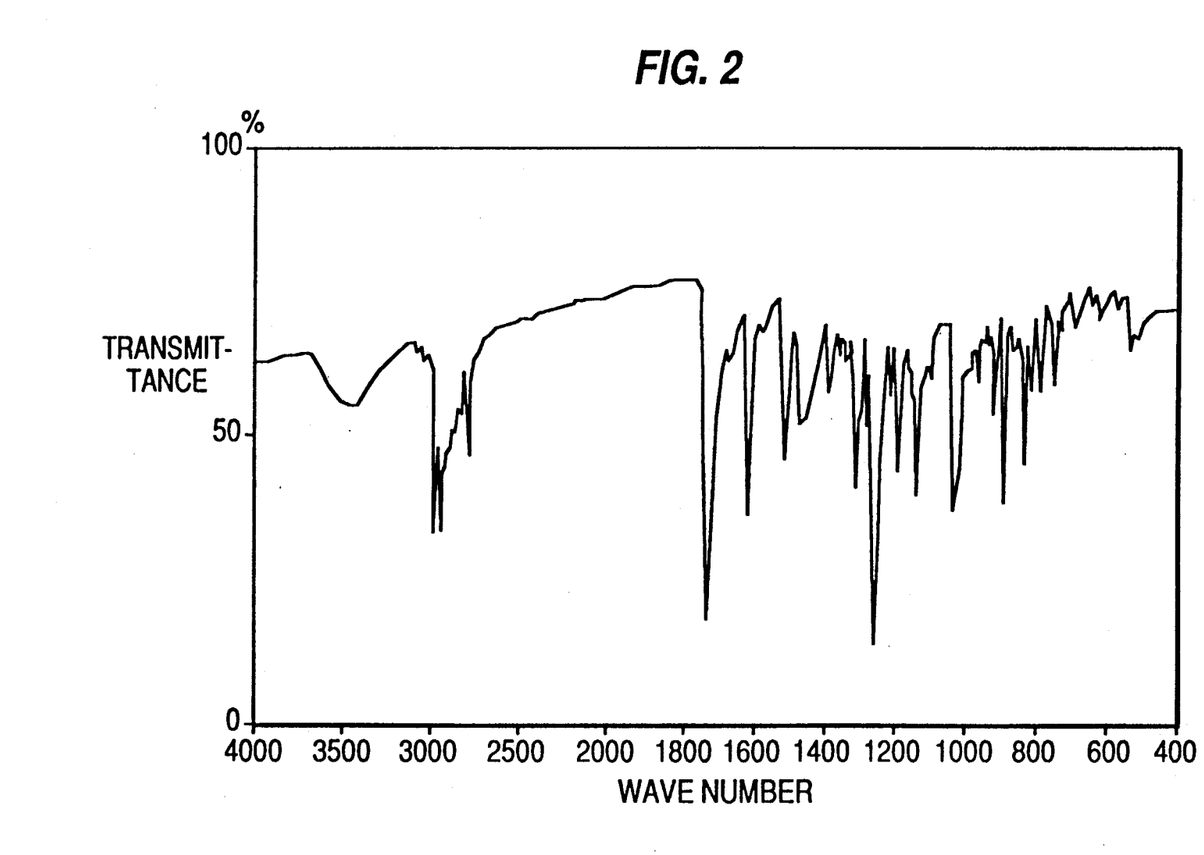
FIG. 2 shows an IR spectrum of TAN-1251A.
Figure 3:
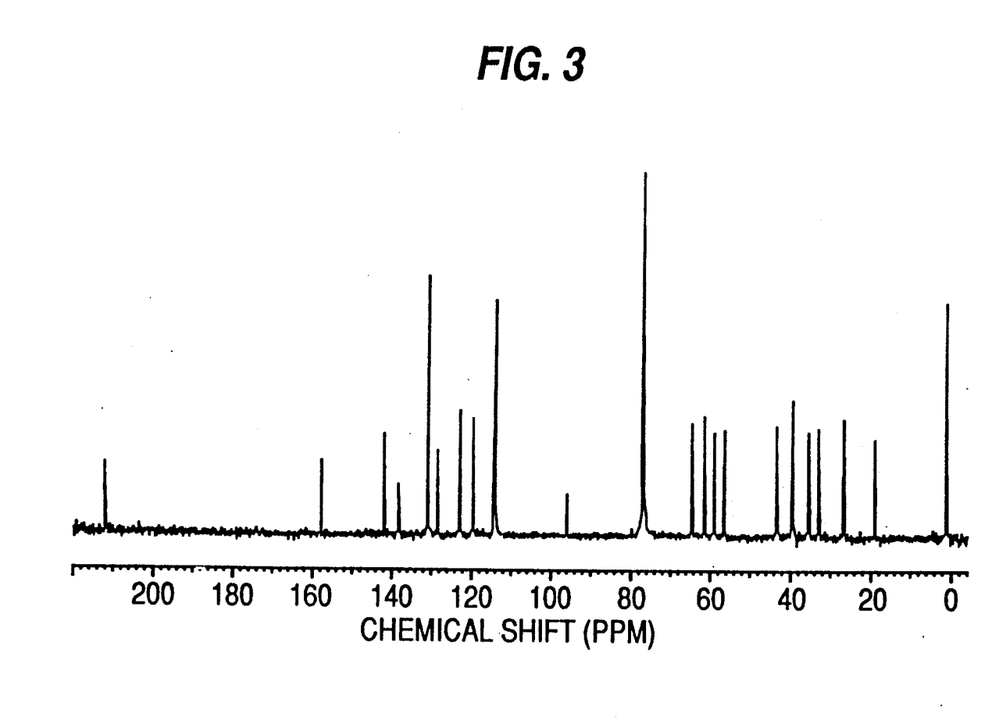
FIG. 3 shows a $^{13}C$ NMR spectrum of TAN-1251A.

TAN-1251A (1) Appearance: Colorless crystals
(2) Melting point: 118.5°–120° C.
(3) Specific rotation: −8.1° (D line, c 0.42, methanol)
(4) Molecular weight: m/z 381 (M+H)+, (SI-mass spectrum)
(5) Elemental analysis: (%)(for the hemihydrate) Found: C, 73.83; H, 8.56; N, 6.92 Calcd.: C, 74.00; H, 8.54; N, 7.19
(6) Molecular formula: $C_{24}H_{32}N_2O_2$
(7) UV spectrum: Methanol (FIG. 1) Absorption maxima: 265±3 nm ($\epsilon$23,800±3,000) 304±3 nm ($\ominus$1,600±400, shoulder)
(8) IR spectrum: KBr disk (FIG. 2); dominant absorptions (wave-number, cm$^{-1}$) 3420, 2980, 2940, 2800, 1720, 1600, 1500, 1450, 1380, 1300, 1250, 1180, 1130, 1030, 920, 890, 830, 780, 750, 690, 620, 530, 510.
(9) $^{13}$C NMR spectrum: 75 MHz, CDCl$_3$, $\epsilon$ ppm; (FIG. 3) 211.95(Q), 157.90(Q), 141.38(Q), 138.14(Q), 130.75(CH), 128.50(Q), 123.01(CH), 119.69(CH), 114.09(CH), 64.65(CH$_2$), 64.07(Q), 61.15(CH), 58.41(CH$_2$), 55.62(CH$_2$), 42.44(CH$_3$), 38.62(CH$_2$), 38.56(CH$_2$), 38.22(CH$_2$), 34.62(CH$_2$), 32.23(CH$_2$), 25.82(CH$_3$), 18.21(CH$_3$). [CH$_3$=methyl, CH$_2$=methylene, CH=methine, Q=quaternary carbon]
(10) Color reactions:
Positive: Dragendorff, phosphomolybdic acid and ninhydrin reactions
Negative: Greig-Liebach reaction
(11) HPLC:
Stationary phase: ODS, YMC-Pack A-312 (YMC)
Mobile phase: 35% Acetonitrile-0.05M sodium phosphate solution (pH3.0)
Flow rate: 2 ml/min
Detection: UV spectrophotometry (214 & 254 nm)
Elution time: 6.9 min.
(12) TLC:
Stationary phase: Silica gel 60 F$_{254}$ (E. Merck, W. Ger.)
Developing solvent: Chloroform-methanol (19:1)
Rf: 0.30
(13) Properties: Basic and liposoluble

Figure 4:
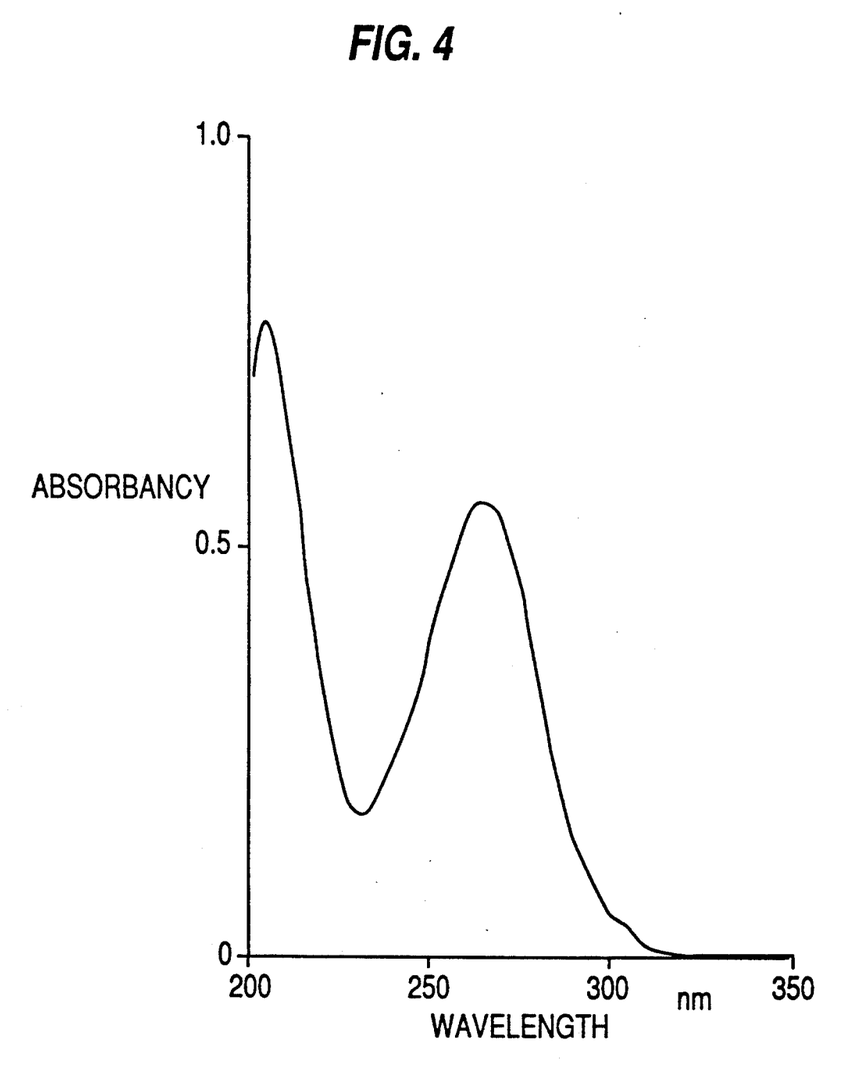
FIG. 4 shows an UV spectrum of TAN-1251B.

TAN-1251B (1) Appearance: Solid
(2) Specific rotation: +65° (D line, C 0.41, methanol)
(3) Molecular weight: m/z 397 (M+H)+, (SI-mass spectrum)
(4) Elemental analysis: (%) (for the hemihydrate) Found: C, 71.35; H, 8.03; N, 6.84 Calcd.: C, 71.08; H, 8.20; N, 6.91
(5) Molecular formula: $C_{24}H_{32}N_2O_3$
(6) UV spectrum: Methanol, (FIG. 4) Absorption maxima: 265±3 nm ($\epsilon$22,700±3,000) 304±3 nm ($\delta$1,700±400, shoulder)

Figure 5:
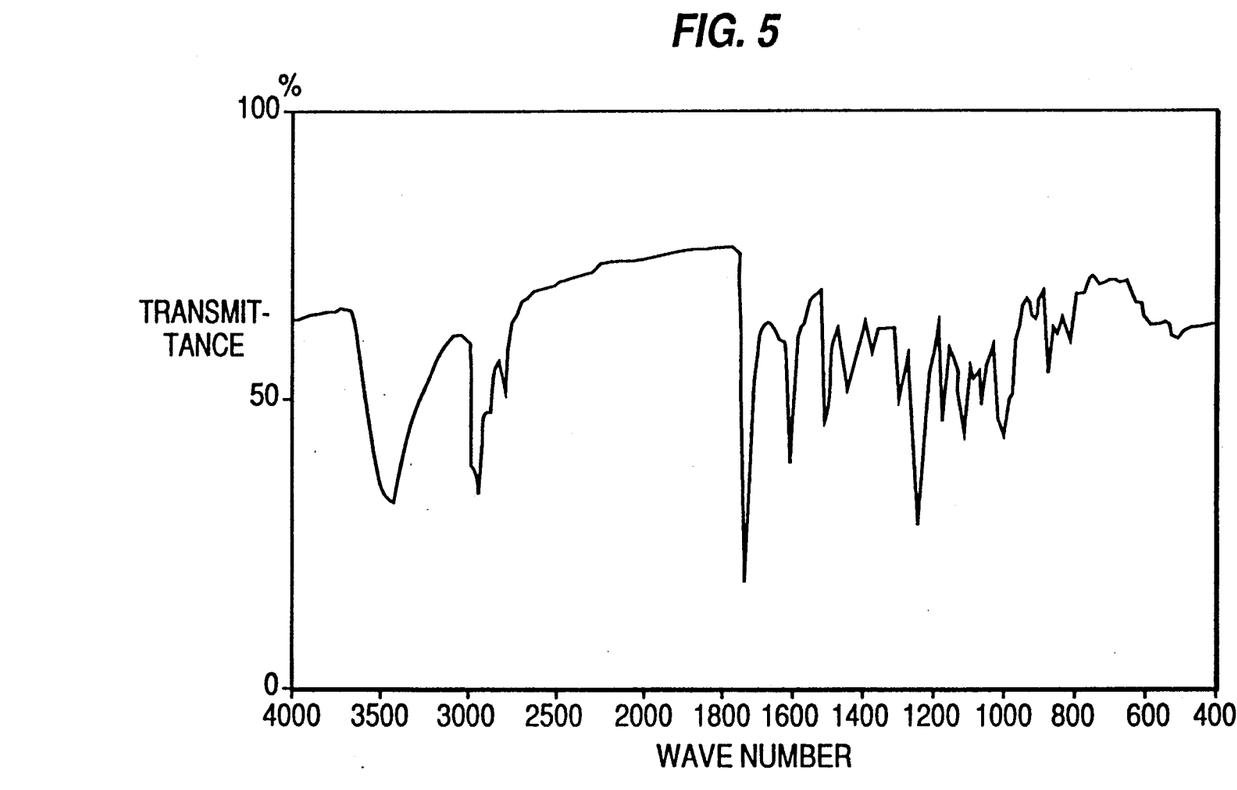
FIG. 5 shows an IR spectrum of TAN-1251B.

(7) IR spectrum: KBr disk (FIG. 5); dominant absorptions (wave-number, cm$^{-1}$) 3430, 2940, 2780, 1720, 1600, 1500, 1440, 1380, 1290, 1240, 1170, 1110, 1060, 1000, 920, 880, 850, 820, 580, 520.

(8) $^{13}$C NMR spectrum: 75 MHz, CDCl$_3$, δ ppm; (FIG. 6) 211.74(Q), 157.96(Q), 141.17(Q), 138.24(Q), 130.67(CH), 128.22(Q), 123.21(CH), 119.59(CH), 114.21(CH), 72.40(CH), 65.30(Q), 64.68(CH$_2$), 60.97(CH), 58.76(CH$_2$), 55.41(CH$_2$), 47.13(CH$_2$), 42.44(CH$_3$), 36.25(CH$_2$), 34.86(CH$_2$), 33.07(CH$_2$), 24.82(CH$_3$), 18.22(CH$_3$).

(9) Color reactions:
Positive: Dragendorff, phosphomolybdic acid and ninhydrin reactions
Negative: Greig-Liebach reaction (10) HPLC:
Stationary phase: ODS, YMC-Pack A-312
Mobile phase: 35% Acetonitrile-0.05M sodium phosphate solution (pH 3.0)
Flow rate: 2 ml/min
Detection: UV spectrophotometry (214 & 254 nm)
Elution time: 3.8 min.

(11) TLC:
Stationary phase: Silica gel 60 F254
Developing solvent: Chloroform-methanol (19:1)
Rf: 0.24

(12) Properties: Basic and liposoluble

TAN-1251C (1) Appearance: Oil
(2) Specific rotation: +24° (D line, c 0.44, methanol)
(3) Molecular weight: m/z 380 M$^+$ (EI-mass spectrum)
(4) Elemental analysis: (%) (for the hemihydrate) Found: C, 74.01; H, 8.40; N, 7.28 Calcd.: C, 74.00; H, 8.54; N, 7.19
(5) Molecular formula: C$_{24}$H$_{32}$N$_2$O$_2$
(6) UV spectrum: Methanol Absorption maxima: 225±3 nm (ε7,800±500) 278±3 nm (ε1,400±400, shoulder) 285±3 nm (ε1,100±300, shoulder)
(7) IR spectrum: KBr disk; dominant absorptions (wave-number, cm$^{-1}$) 3430, 2950, 2880, 1720, 1680, 1640, 1610, 1510, 1450, 1370, 1320, 1300, 1240, 1170, 1120, 1050, 1000, 860, 840, 810, 790, 730, 630, 510.
(8) $^{13}$C NMR spectrum: 75 MHz, CDCl$_3$, δ ppm; 221.54(Q), 157.16(Q), 137.84(Q), 131.95(Q), 129.82(CH), 128.12(Q), 127.80(CH), 119.94(CH), 114.40(CH), 71.42(Q), 64.72(CH$_2$), 59.05(CH), 52.20(CH$_2$), 42.94(CH$_2$), 41.44(CH$_2$), 40.29(CH$_3$), 39 50(CH$_2$), 37.80(CH$_2$), 37.25(CH$_2$), 34.59(CH$_2$), 25.81(CH$_3$), 18.19(CH$_3$)

(9) Color reactions:
Positive: Dragendorff, phosphomolybdic acid and ninhydrin reactions Negative: Greig-Liebach reaction (10) HPLC:
Stationary phase: ODS, YMC-Pack A-312
Mobile phase: 35% Acetonitrile-0.05M sodium phosphate solution (pH 3.0)
Flow rate: 2 ml/min
Detection: UV spectrophotometry (214 & 254 nm)
Elution time: 9.3 min.

(11) TLC:
Stationary phase: Silica gel 60 F254
Developing solvent: Chloroform-methanol (19:1)
Rf: 0.80

(12) Properties: Basic and liposoluble

TAN-1251D (1) Appearance: Oil
(2) Specific rotation: +24° (D line, c 0.47, methanol)
(3) Molecular weight: m/z 382 M$^+$ (EI-mass spectrum)
(4) Elemental analysis: (%) (for the hemihydrate) Found: C, 73.66; H, 8.92; N, 7.28 Calcd.: C, 73.62; H, 9.01; N, 7.15
(5) Molecular formula: C$_{24}$H$_{34}$N$_2$O$_2$
(6) UV spectrum: Methanol Absorption maxima: 226±3 nm (ε7,800±1,500) 275±3 nm (ε1,600±400, shoulder) 284±3 nm (ε1,200±300, shoulder)
(7) IR spectrum: KBr disk; dominant absorptions (wave-number, cm$^{-1}$) 3420, 2970, 2940, 2880, 2800, 1720, 1610, 1510, 1450, 1380, 1340, 1300, 1240, 1180, 1150, 1110, 1060, 1020, 1000, 950, 910, 850, 830, 810, 770, 730, 680, 640, 510.
(8) $^{13}$C NMR spectrum: 75 MHz, CDCl$_3$, δ ppm; 210.86(Q), 158.43(Q), 137.96(Q), 131.89(Q), 129.76(CH), 119.82(CH), 114.70(CH), 65.78(CH), 64.98(Q), 64.78(CH$_2$), 61.88(CH$_2$), 61.31(CH), 52.30(CH$_2$), 42.42(CH$_3$), 41.39(CH$_2$), 39.63(CH$_2$), 39.22(CH$_2$), 37.97(CH$_2$), 33.27(CH$_3$), 33.02(CH$_2$), 25.81(CH$_3$), 18.18(CH$_3$)

(9) Color reactions:
Positive: Dragendorff, phosphomolybdic acid and ninhydrin reactions
Negative: Greig-Liebach reaction (10) HPLC:
Stationary phase: ODS, YMC-Pack A-312
Mobile phase: 35% Acetonitrile-0.05M sodium phosphate solution (pH 3.0)
Flow rate: 2 ml/min
Detection: UV spectrophotometry (214 & 254 nm)
Elution time: 3.2 min.

(11) TLC:
Stationary phase: Silica gel 60 F254
Developing solvent: Chloroform-methanol (19:1)
Rf: 0.18

(12) Properties: Basic and liposoluble

The compound numbers and chemical structures of the compounds mentioned in the description and examples are as follows.

| Compound No. | Chemical structure |
|---|---|
| 1 | (structure) |
| 2 | (structure) |

-continued

| Compound No. | Chemical structure |
|---|---|
| 3 | (structure) |
| 4 | (structure) |
| 5 | (structure) ·½H₂SO₄ |
| 6 | (structure) ·½H₂SO₄ |
| 7 | (structure) |
| 8 | (structure) |
| 9 | (structure) |
| 10 | (structure) |
| 11 | (structure) |
| 12 | (structure) |
| 13 | (structure) |
| 14 | (structure) |
| 15 | (structure) |

-continued

| Compound No. | Chemical structure |
|---|---|
| 16 | [structure showing a compound with prenyloxy-phenyl group, N-CH3, N-ethyl, cyclohexanone with OCOCH3 substituent] |

(Compounds 9 and 10 and Compounds 11 and 12 are stereoisomers in the position *)

Compounds of general formula (I) can be synthesized from TAN-1251A, B, C and D by conducting the ether bond cleaving reaction with an acid, carbonyl reduction reaction, catalytic double bond reduction, quaternization reaction by alkylation of tertiary amine, hydroxyl acylation reaction, and/or reaction for introduction of a hydrocarbon group into the OH group of phenol in the per se conventional manner.

The above procedures are now described in detail taking the above-mentioned Compounds 1 through 16 as examples.

The conversion of Compound 1 to Compound 7, or Compound 2 to Compound 8, is best performed under acidic conditions. Thus, the starting compound is dissolved in 0.1~2.0N, preferably 0.2~1.0N, hydrochloric acid or sulfuric acid at a final concentration of 2~50 mg/ml, preferably 5~30 mg/ml, and allowed to react at a temperature of 4°~80° C., preferably 10°~40° C., for 30 minutes to 2 days, preferably 1~8 hours.

The conversion of Compound 1 to Compounds 9 and 10, or Compound 2 to Compounds 11 and 12, is most advantageously carried out using sodium borohydride. Thus, the starting compound is dissolved in methanol, ethanol or tetrahydrofuran at a final concentration of 5~100 mg/ml, preferably 10~50 mg/ml, and after addition of 0.2~10 equivalents, preferably 1~5 equivalents, of sodium borohydride, the reaction is carried out at 4°~80° C., preferably 10°~40° C., for 30 seconds~5 hours, preferably 5 minutes to 1 hour. Other reducing agents such as sodium cyanoborohydride, lithium aluminum hydride, etc. can also be employed in lieu of sodium borohydride.

The conversion of Compound 1 to Compound 13, or Compound 2 to Compound 14, can be effectively carried out by catalytic reduction. Thus, the starting compound is dissolved in methanol or ethanol at a final concentration of 2~50 mg/ml, preferably 5~20 mg/ml and, after addition of a catalytic amount (2~60%, preferably 10~50% by weight) of palladium black, palladium-on-carbon, platinum black or platinum dioxide, the reaction is carried out in a hydrogen gas atmosphere at 4°~80° C., preferably 10°~40° C., for 1 hour~2 days, preferably 2~8 hours.

The conversion of Compound 2 to Compound 15 can be carried out most advantageously using methyl iodide. Thus, the starting compound is dissolved in methanol, ethanol or propanol at a final concentration of 5~200 mg/ml, preferably 10~100 mg/ml and, after addition of 1~10 equivalents, preferably 1.1~6 equivalents, of methyl iodide, the reaction is carried out at a temperature of 20°~100° C., preferably 60°~80° C., for 30 minutes to 5 hours, preferably 1~2 hours.

The conversion of Compound 2 or 6 to Compound 16 is most effectively carried out using acetic anhydride and pyridine. Thus, the starting compound is dissolved in pyridine at a final concentration of 10~1000 mg/ml, preferably 20~500 mg/ml and, after addition of 1 or more equivalents of acetic anhydride, the reaction is conducted at 4°~80° C., preferably 10°~40° C., for 1 hour~3 days, preferably 5 hours~2 days.

Compound 7 or 8 has a phenolic hydroxyl group(s) and, as such, gives an ether derivative as described hereinafter. Thus, for the introduction of an alkyl group into the acidic group of phenol or the like, the following procedures, for instance, are known and can be adequately applied to the production of compounds of the invention.

1) The starting compound is reacted with a diazoalkane (e.g. diazomethane) in a solvent (e.g. ethyl ether, tetrahydrofuran, dioxane, methanol, etc.) at a temperature between about 0° C. and the reflux temperature for a period of about 2 minutes~10 hours.

2) The starting compound is reacted with an active alkyl halide (e.g. methyl iodide, n-butyl chloride, etc.). Referring to suitable conditions, the reaction is conducted in a solvent (e.g. dimethylformamide, dimethylacetamide, etc.) at a temperature of about 0°~60° C. for about 2 minutes~20 hours. The presence of an alkali metal salt (e.g. sodium carbonate, potassium carbonate, etc.), ammonia, triethylamine or the like in the reaction system does not interfere with the reaction.

3) The starting compound is reacted with an alcohol (e.g. methanol, n-butanol, etc.). Preferably this reaction is conducted in a solvent (e.g. dimethylformamide etc.) in the presence of a condensing agent (e.g. dicyclohexylcarbodiimide) at a temperature of about 0°~60° C. for about 2 hours~2 days. The reaction system may contain an auxiliary condensing agent (e.g. 1-hydroxy-1H-benzotriazole etc.).

The following microbial transformation technique may be advantageously employed in combination with the various transformation reactions described above.

The hydroxylation of a compound of general formula (I) wherein $R^3$ H to a compound wherein $R^3$ is OH can be carried out with the aid of a microorganism belonging to the genus Penicillum. This reaction can be conducted in a medium favoring growth of the microorganism or in the presence of a processed culture broth such as washed cells, immobilized cells and so on. A specific example is presented in Example 13, where the microbial transformation of TAN-1251A into TAN-1251B was carried out using *Penicillium thomii* RA-89.

The biological activity of TAN-1251 is shown below. The assay of activity was carried out by the following two methods.

(1) Muscarinic receptor-radio receptor assay

This assay was carried out in accordance with the method of R.F.T. Gilbert et al. [British Journal of Pharmacology 65, 451 (1979)]. A Wistar rat (male, 8 weeks old, Clea Japan, Inc.) was decapitated and the brain was isolated. The cerebral cortex was then separated and using a Teflon homogenizer, the whole cerebral cortex (0.8~1.0 g) was homogenized in 30 ml of 0.32M sucrose solution. The homogenate was centrifuged at 1,000G for 10 minutes and the supernatant was re-centrifuged at 20,000G for 20 minutes. The pellet was used as a crude receptor membrane fraction (P2 fraction). In the binding assay, the P2 fraction was suspended in 30 ml of 0.1M sodium potassium phosphate buffer (protein concentration: 0.5 mg/ml) and diluted 50~80-fold with the same buffer. A 200 μl portion of this dilution was used in the assay. As a radioligand, $^3$H-QNB (1.63 TBq/mmol, Amersham, U.K.) was added at the level of 0.148 KBq and the sample was added at the same time. The reaction was carried out at room temperature for 60 minutes. Then, using a cell harvester (290 PHD, Cambridge Technology, Inc., U.K.), the reaction mixture was subjected to rapid filtration through a glass filter (GF/B, Whatman, U.S.A.) to terminate the reaction and after washing with three 300 μl portions of the same buffer as above, the residual radioactivity on the filter was measured with a liquid scintillation counter. The activity was expressed in the number of units representing the reciprocal of the sample size (ml) required for 50% inhibition or in the corresponding concentration (M), viz. $IC_{50}$.

(b) Antagonizing activity against acetylcholine-induced contraction of the isolated Guinea pig ileum A Guinea pig (Std Hartley, male, 250 g, Japan SLC) deprived of food for 24 hours was subjected to brain concussion and after exsanguination from the carotid artery, the ileum was isolated. An ileal strip, about 3 cm long, was prepared and suspended in a Magnus tube containing 20 ml of Tyrode solution. At a constant bath temperature of 37° C., a mixed gas (95% $O_2$–5% $CO_2$) was bubbled through the bath. The sample was added and after 5 minutes of equilibration, acetylcholine (Daiichi Seiyaku, Japan) was added at a final concentration of $1 \times 10^{-7}$ M to induce contraction of the ileal strip. The contraction was recorded through an isotonic transducer (ME-4013, Suruga Electronics, Japan) on a recorder (Rectiholy 8K, Japan Electronics Sanei, Japan). The activity of the same was expressed in $ED_{50}$ representing 50% inhibition of the maximal contraction.

The results of the above tests with TAN-1251A and B are shown in Table 3.

TABLE 3

| | Biological activity of TAN-1251 | |
|---|---|---|
| Compound | a. Radio receptor assay $IC_{50}$ (M) | b. Guinea pig ileal contractility $ED_{50}$ (M) |
| 1 | $5.7 \times 10^{-9}$ | $8.0 \times 10^{-9}$ |
| 2 | $1.3 \times 10^{-10}$ | $1.3 \times 10^{-8}$ |

It will be apparent from Table 3 that TAN-1251 showed very high inhibitory activity. This anti muscarinic activity was comparable to that of atropine.

For assessment of the acute toxicity of TAN-1251, an oral administration experiment using TAN-1251A and B was performed in mice. As a result, no toxic signs were observed at the dose level of 100 mg/kg for either substance.

It will be apparent from the physiochemical and biological properties described above that TAN-1251 is a novel compound and that, as an antimuscarinic agent, it is of value as a therapeutic drug for various diseases such as gastric and duodenal ulcers, spastic pain of the gastrointestinal tract, parkinsonism, etc. or as a mydriatic.

TAN-1251 or a salt thereof is administered orally or parenterally as an injectable preparation. The oral dosage for humans is generally 0.05~50 mg/kg/day, preferably 0.1~10 mg/kg/day, and the parenteral dosage is 0.01~10 mg/kg/day, preferably 0.05~5 mg/kg.

The dosage form for oral administration includes, inter alia, capsules, tablets, granules, syrups, powders, etc. and may contain, in addition to TAN-1251 or a salt thereof, such additives as various excipients, binders, disintegrators, lubricants, colorants, corrigents, stabilizers and so on.

For parenteral administration, the active compound can be dissolved or suspended in the common diluent (an aqueous or non-aqueous vehicle) and provided in a variety of pertinent dosage forms such as solutions, eye drops, emulsions, suspensions, suppositories and so on. In the manufacture of such pharmaceutical compositions, there may be employed a diversity of additives such as emulsifiers, suspending agents, cosolvents, stabilizers, preservatives, soothing agents, isotonizing agents, buffers, pH adjusting agents, colorants, coating agents and so on. These pharmaceutical compositions or preparations can be manufactured by the established pharmaceutical procedures.

EXAMPLES

The following examples are merely intended to illustrate the invention in further detail and should by no means be construed as defining the metes and bounds of the invention. It should be noted that all percents (%) relating to media are weight/volume percents unless otherwise indicated.

EXAMPLE 1

*Penicillium thomii* RA-89 (IFO-32288, FERM BP-2753) grown on a slant agar medium composed of 24 g potato dextrose broth (Difco, U.S.A.), 20 g agar and 1 l water at 28° C. for 7 days was inoculated into 40 ml of a seed medium (pH 6.5) composed of 2% glucose, 3% maltose, 1% raw soybean flour (SBF), 0.5% corn steep liquor (CSL), 0.25% peptone, 0.15% yeast extract and 0.15% NaCl. The inoculated medium in a 200 ml conical flask was incubated on a rotary shaker at 24° C. for 48 hours to provide a preculture. The whole amount of this preculture was transferred to a 2000 ml Sakaguchi flask containing 500 ml of the seed culture medium and incubated on a reciprocating shaker at 24° C. for 24 hours to provide a seed culture. A 1000 ml portion of the seed culture obtained in the above manner was transferred to a 200 liter stainless steel tank containing 120 l of a fermentation medium (pH 6.7) containing 5% of glycerol, 2.5% of sucrose, 1% of SBF, 0.5% of peptone, 0.2% of malt extract, 0.1% of yeast extract, 0.2% of ammonium sulfate, 0.5% of calcium carbonate and 0.05% of Aktocol (Takeda Chemical Industries, Ltd., Japan). The inoculated medium was incubated at 24° C., with aeration at a rate of 150 l/min. and agitation at 200 rpm and under an internal pressure of 1 kg/cm$^2$ for 90 hours. As found by radio receptor assay of TAN-1251 in the culture supernatant, its output was 45,000 units.

EXAMPLE 2

To the culture broth (100 l) was added Hyflo Super-Cel (Johns-Manville Corporation, U.S.A.) as a filter aid and the mixture was filtered. After the filtrate was adjusted to pH 8.0, the bioactive substance was extracted with ethyl acetate (70 l). The organic layer was extracted with 0.01N hydrochloric acid (50 l) and the aqueous solution was adjusted to pH 8.0 and re-extracted with ethyl acetate (33 l). The organic layer was washed with water (23 l) and concentrated to give a crude oil (1.09 g). It was combined with the crude oil (0.99 g) obtained in the same manner and the pooled oil was dissolved in chloroform and subjected to silica gel (100 g) column chromatography. The bioactive components were eluted successively with chloroform-methanol mixtures, (99.1, 3.5 l) (98.2, 2.0 l) and (95:5, 0.5 l), the respective fractions were analyzed by HPLC, and the fractions containing either TAN-1251A or TAN-1251B only were respectively pooled and concentrated to dryness.

The oil containing TAN-1251A (0.27 g) was combined with the oil containing TAN-1251A (1.8 g) obtained in the same manner and the pooled oil was subjected to preparative HPLC [stationary phase YMC-Pack S-363 I-15 (YMC, Japan), mobile phase 32% acetonitrile/0.01M sodium phosphate (pH 3.0)]. The eluate was analyzed by HPLC and the fractions containing TAN-1251A were pooled. A portion (1.4 l) of this solution was concentrated to 0.3 l, adjusted to pH 8.0 and extracted with ethyl acetate (200 ml). The resulting organic layer was washed with water and concentrated to dryness to recover a powder of TAN-1251A (300 mg). This powder (130 mg) was recrystallized from ethyl acetate to provide colorless crystals of TAN-1251A (51 mg).

The oil containing TAN-1251B (0.49 g) was combined with the oil containing TAN-1251B (0.33 g) obtained in the same manner and the pooled oil was subjected to preparative HPLC [stationary phase YMC-Pack S-363 I-15, mobile phase 25% acetonitrile/0.01M sodium phosphate (pH 3.0)]. The eluate was analyzed by HPLC and the fractions containing TAN-1251B were pooled. A portion (500 ml) of this solution was concentrated to 100 ml, adjusted to pH 8.0 and extracted with ethyl acetate (150 ml). The extract was washed with water and concentrated to dryness to provide a powder of TAN-1251B (132 mg).

EXAMPLE 3

The solution containing TAN-1251A (1.4 l) obtained by preparative HPLC in Example 2 was concentrated and passed through a column of Amberlite IRA-402 ($SO_4^{2-}$-form, 0.3 l, Rohm and Haas Company, U.S.A.). The effluent and the aqueous wash were chromatographed on Amberlite XAD-II (60 ml) and the activity was eluted with 50% aqueous methanol (240 ml) and 70% aqueous acetone (300 ml). The eluate was concentrated and freeze-dried to provide a white powder of TAN-1251A sulfate (667 mg).

Similarly, the solution containing TAN-1251B (280 ml) obtained by preparative HPLC in Example 2 was chromatographed using Amberlite IRA-402 ($SO_4^{2-}$-form, 50 ml) and Amberlite XAD-II (20 ml) and the eluate was concentrated and freeze-dried to provide a white powder of TAN-1251B sulfate (114 mg).

TAN-1251A sulfate

Specific rotation: $-14°$ (D line, c 0.23, 50% aqueous methanol, 22° C.)

UV: Absorption maxima in $H_2O$: 266 nm ($\epsilon$24,200), 303 nm ($\epsilon$1,900, shoulder) IR: KBr disk, dominant absorptions (wave-number, $cm^{-1}$): 3430, 2960, 1720, 1600, 1500, 1450, 1240, 1120, 1000, 830, 620

Elemental analysis (for $C_{24}H_{32}N_2O_2 \cdot 0.5H_2SO_4 \cdot 2 H_2O$) Calcd.: C, 61.91: H, 8.01; N, 6.02; S, 3.44 Found: C, 62.10; H, 7.97; N, 5.85; S, 3.19

TAN-1251B sulfate

Specific rotation: $+67°$ (D line, c 0.24, 50% aqueous methanol, 22° C.)

UV: Absorption maxima in $H_2O$: 264 nm ($\epsilon$25,200), 303 nm ($\epsilon$1,400, shoulder LR: KBr disk, dominant absorptions (wave-number, $cm^{-1}$): 3430, 2950, 1720, 1600, 1500, 1450, 1240, 1120, 1010, 620

Elemental analysis (for $C_{24}H_{32}N_2O_3 \cdot 0.5H_2SO_4 \cdot 1.5-H_2O$) Calcd.: C, 61.00; H, 7.68; N, 5.93; S, 3.39 Found: C, 61.30; H, 7.85; N, 5.92; S, 3.12

EXAMPLE 4

The spores formed on the same slant as used in Example 1 were suspended in 10 ml of water and the whole amount was transferred to a 2 l Sakaguchi flask containing 500 ml of a seed medium and incubated on a reciprocating shaker at 24° C. for 48 hours to give a preculture. One liter portion of the preculture was transferred to a 200 l stainless steel tank containing 100 l of a seed medium (with 0.05% Aktocol added) and incubated at 24° C. with aeration at a rate of 120 l/min. and agitation at 150 rpm under an internal pressure of 1 $kg/cm^2$ for 48 hours. A 50 l portion of the resulting seed culture was transferred to a 6,000 l stainless steel thank containing 3,600 l of the same fermentation medium as used in Example 1 and incubated at 24° C. with aeration at a rate of 3,600 l/min. and agitation at 200 rpm under an internal pressure of 1 $kg/cm^2$ for 90 hours. The culture supernatant contained 110,000 units of TAN-1251.

The culture broth (3,480 l) was subjected to Oliver filtration using Radiolite (Showa Chemical Industry, Japan) as a filter aid. The filtrate was adjusted to pH 6.5 and passed through a column of Diaion HP-20 (70 l, Mitsubishi Kasei, Japan). The column was washed with water (210 l) and 30% aqueous methanol (210 l) in that order and elution was carried out with 60% acetone/0.01N sulfuric acid (280 l). The eluate was adjusted to pH 4.2 and concentrated to remove the acetone. The resulting aqueous solution (80 l) was adjusted to pH 8.4 and extracted with ethyl acetate (40 l×2). The extract was washed with water (25 l×2) and concentrated to 5 l and the concentrate was extracted with 0.02N hydrochloric acid (2 l×2). The solution was adjusted to pH 3.4, concentrated and subjected to Diaion HP-20 (50~100 mesh, 0.7 l) column chromatography. The column was washed with water (2 l) and 20% aqueous methanol (2 l), followed by elution with 50% aqueous methanol (2.1 l), 60% aqueous acetone (2.1 l) and 70% acetone/0.01N hydrochloric acid (2.1 l) in the order mentioned. The fraction eluted by 70% acetone/0.01N hydrochloric acid was concentrated to 400 ml for removal of the acetone and the concentrate was adjusted to pH 8.2 and extracted with ethyl acetate (200 ml×2). The extract was washed with water (150 ml×2) and concentrated to dryness. The residue was subjected to silica gel (100 ml; solvent system: chloroform-methanol) column chromatography. The fractions containing TAN-1251A were pooled and concentrated to dryness and the resulting powder was crystallized from ethyl acetate-hexane to provide crystals of TAN-1251A (925 mg).

The eluate obtained with 50% aqueous methanol and that obtained with 60% aqueous acetone from the Diaion HP-20 column and concentrated and the concentrate was adjusted to pH 8.2 and extracted with ethyl acetate. The extract was washed with water, concentrated to dryness and subjected to silica gel (200 ml; solvent system: chloroform-methanol) column chromatography. The fractions rich in TAN-1251B, C and D, respectively, were taken independently and concentrated to dryness to provide an oil containing TAN-1251C (1.3 g) and an oil containing TAN-1251D (2.0 g).

The fraction containing TAN-1251B was concentrated to dryness and crystallized to give crystals of TAN-1251B (1.2 g).

The oil containing TAN-1251C (1.3 g) and the oil containing TAN-1251C obtained in the same manner (4.3 g) were combined and purified by silica gel (300 ml; solvent system: dichloroethane-methanol) column chromatography to give TAN-1251C (5.1 g). The oil containing TAN-1251D (2.0 g) and the oil containing TAN-1251D (8.1 g) obtained in the same manner were combined and purified by silica gel (500 ml; solvent system: dichloroethane-methanol) column chromatography to provide TAN-1251D (7.6 g).

EXAMPLE 5

Compound 1 (109 mg) was dissolved in 0.5N hydrochloric acid (10 ml) and the solution was allowed to stand at room temperature for 5 hours. The reaction mixture was then adjusted to pH 8.5 and extracted with ethyl acetate. The insoluble matter which separated out in this extraction step was recovered by filtration to provide Compound 7 (49 mg). The organic layer was washed with water, dehydrated over anhydrous sodium sulfate and concentrated to dryness to give a further crop of Compound 7 (36 mg).

Specific rotation: −8.1° (D line, c 0.41, methanol, 25° C.)

UV: Absorption maxima in methanol: 264 mm ($\epsilon$22,000), 303 nm ($\epsilon$1,700, shoulder)

IR: KBr disk, dominant absorptions (wave-number, $cm^{-1}$): 3520, 2970, 2940, 1705, 1610

EI-MS: 312 (M+)

Elemental analysis (for $C_{19}H_{24}N_2O_2 \cdot H_2O$) Calcd.: C, 69.07; H, 7.93; N, 8.48 Found: C, 69.46; H, 7.92; N, 8.09

$^{13}C$ NMR spectrum (75 MHz, $CD_3OD$, δ ppm): 214.58(Q), 157.75(Q), 141.69(Q), 132.07(CH×2), 128.73(Q), 124.66(CH), 115.72(CH×2), 65.20(Q), 62,46(CH), 58.75($CH_2$), 56.21($CH_2$), 42.43($CH_3$), 39.34($CH_2$×2), 38.65($CH_2$), 35.63($CH_2$), 32.94($CH_2$)

EXAMPLE 6

Command 2 (578 mg) was dissolved in 0.5N hydrochloric acid (30 ml) and the solution was stirred at room temperature for 2.5 hours. The reaction mixture was then adjusted to pH 8.5, diluted with a saturated aqueous solution of sodium chloride, and extracted with ethyl acetate. The organic layer was washed with a saturated aqueous solution of sodium chloride, dehydrated over anhydrous sodium sulfate and concentrated to dryness. The residue was tritulated with ethyl acetate-hexane to provide Compound 8 (446 mg).

Specific rotation: +81.9° (D line, c 0.42, methanol, 25° C.)

UV: Absorption maxima in methanol: 262 nm ($\epsilon$22,500), 303 nm ($\epsilon$1,600, shoulder)

IR: KBr disk, dominant absorptions (wave-number, $cm^{-1}$): 3430, 2950, 1725, 1610 EI-MS: 328(M+)

Elemental analysis (for $C_{19}H_{24}N_2O_3$) Calcd.: C, 69.49; H, 7.37; N, 8.53 Found: C, 68.75; H, 7.25; N, 8.42

$^{13}C$ NMR spectrum (75 MHz, $CDCl_3$, δ ppm): 211.63(Q), 156.08(Q), 139.73(Q), 130.98(CH×2), 127.23(Q), 123.97(CH), 115.35(CH×2), 72.40(CH), 65.26(Q), 60.86(CH), 57.96($CH_2$), 55.05($CH_2$), 46.84($CH_2$), 42.13($CH_3$), 36.28($CH_2$), 35.13($CH_2$), 33.00($CH_2$).

EXAMPLE 7

Compound 1 (180 mg) was dissolved in ethanol (6 ml) followed by addition of sodium borohydride (60 mg) and the mixture was stirred at room temperature for 30 minutes. The reaction mixture was adjusted to pH 2.5 with diluted hydrochloric acid and washed with ethyl acetate. The aqueous layer was adjusted to pH 8.5 and extracted with ethyl acetate. The organic layer was washed with a saturated aqueous solution of sodium chloride, dehydrated over anhydrous sodium sulfate and concentrated to dryness to provide a crude powder containing Compounds 9 and 10 (184 mg). This crude powder was subjected to preparative HPLC [stationary phase: YMC-Pack D-ODS-5 (YMC), mobile phase: 28% acetonitrile-0.02M sodium phosphate (pH 3)]. The eluate was analyzed by HPLC and the fractions containing 9 and 10, respectively, were independently pooled. Each of the solutions thus obtained was concentrated, adjusted to pH 8.5 and extracted with ethyl acetate. The organic layer was washed with a saturated aqueous solution of sodium chloride, dehydrated over anhydrous sodium sulfate and concentrated to dryness to provide Compound 9 (92 mg) and Compound 10 (47 mg).

Compound 9

UV: Absorption maxima in methanol: 265 nm ($\epsilon$29,000), 304 nm($\epsilon$1,900, shoulder)

Elemental analysis (for $C_{24}H_{34}N_2O_2$) Calcd.: C, 75.35; H, 8.96; N, 7.32 Found: C, 75.05; H, 9.22; N, 7.05

$^{13}C$ NMR spectrum (75 MHz, $CDCl_3$, δ ppm): 157.65(Q), 141.91(Q), 137.99(Q), 131.18(CH×2(, 129.13(Q), 122.29(CH), 119.79(CH), 113.87(CH×2), 69.31(CH), 64.67($CH_2$), 64.37(Q), 61.02(CH), 58.10($CH_2$), 55.82($CH_2$), 42.44($CH_3$), 35.84($CH_2$), 34.76($CH_2$), 32.16($CH_2$), 32.05($CH_2$), 29.68($CH_2$), 25.81($CH_3$), 18.20($CH_3$)

HPLC:

Stationary phase: ODS, YMC-Pack A-312

Mobile phase: 35% Acetonitrile-0.05M sodium phosphate solution (pH 3)

Flow rate: 2 ml/min

Detection: UV spectrophotometry (214 & 254 nm)

Elution time: 3.6 min.

Compound 10

UV: Absorption maxima in methanol: 265 nm ($\epsilon$26,400), 304 nm ($\epsilon$2,000, shoulder)

Elemental analysis (for $C_{24}H_{34}N_2O_2 \cdot \frac{1}{2}H_2O$) Calcd.: C, 73.62; H, 9.01; N, 7.15 Found: C, 73.46; H, 9.06; N, 6.78

$^{13}C$ NMR spectrum (75 MHz, $CDCl_3$, δ ppm): 157.61(Q), 141.92(Q), 138.00(Q), 130.90 (CH×2), 129.22(Q), 122.10(CH), 119.81(CH), 113.98(CH×2), 68.83(CH), 64.72($CH_2$), 64.70(Q), 61.12(CH), 57.61($CH_2$), 55.55($CH_2$), 42.42($CH_3$), 35.47($CH_2$), 33.41($CH_2$), 32.61($CH_2$), 31.70($CH_2$), 28.90 ($CH_2$), 25.82($CH_3$), 18.19($CH_3$)

HPLC: The same conditions for Compound 9. Elution time: 4.4 min.

EXAMPLE 8

Compound 2 (178 mg) was dissolved in ethanol (6 ml) followed by addition of sodium borohydride (60 mg) and the mixture was stirred at room temperature for 15 minutes. The reaction mixture was extracted in the same manner as in Example 7 to give a crude powder containing Compounds 11 and 12 (173 mg). This crude powder was subjected to preparative HPLC [stationary phase: YMC-Pack D-ODS-5; mobile phase 22% acetonitrile-0.02M sodium phosphate (pH 3)]. The fractions were treated in the same manner as in Example 7 to provide Compound 11 (127 mg) and Compound 12 (25 mg).

Compound 11

Specific rotation: +45.0° (D line, c 0.46, methanol, 25° C.)

UV: Absorption maxima in methanol: 264 nm ($\epsilon$27,000), 303 nm ($\epsilon$1,900, shoulder)

Elemental analysis (for $C_{24}H_{34}N_2O_3 \cdot H_2O$) Calcd.: C, 69.20; H, 8.71; N, 6.72 Found: C, 69.03; H, 8.36; N, 6.64

$^{13}$C NMR spectrum (75 MHz, CDCl$_3$, $\delta$ ppm): 157.73(Q), 141.27(Q), 137.98(Q), 131.09(CH×2), 128.81(Q), 122.68(CH), 119.74(CH), 113.94(CH×2), 76.05(CH), 73.08(CH), 65.88(Q), 64.69(CH$_2$), 60.87(CH), 58.52(CH$_2$), 55.72(CH$_2$), 44.06(CH$_2$), 42.37(CH$_3$), 35.89(CH$_2$), 30.61(CH$_2$), 29.77(CH$_2$), 25,81(CH$_3$), 18.21(CH$_3$)

HPLC:

Stationary phase: ODS, YMC-Pack A-312

Mobile phase: 35% Acetonitrile-0.02 sodium phosphate solution (pH 3)

Flow rate: 2 ml/min

Detection: UV spectrophotometry (214 & 254 nm)

Elution time: 2.6 min.

Compound 12

Specific rotation: +81.3° (D line, c 0.29, methanol, 25° C.)

UV: Absorption maxima in methanol: 264 nm ($\epsilon$24,600), 303 nm ($\epsilon$1,800, shoulder)

Elemental analysis (for $C_{24}H_{34}N_2O_3 \cdot \frac{1}{2}H_2O$) Calcd.: C, 70,73; H, 8.66; N, 6.87 Found: C, 71.06; H, 8.74; N, 6.70

$^{13}$C NMR spectrum (75 MHz, CDCl$_3$, $\delta$ ppm): 157.64(Q), 141.65(Q), 138.03(Q), 130.84(CH×2), 128.91(Q), 122.49(CH), 119.74(CH), 113.94(CH×2), 69.43(CH), 68.47(CH), 65.95(Q), 64.69(CH$_2$), 60.89(CH), 58.31(CH$_2$), 55.71(CH$_2$), 42.34(CH$_3$), 40.28(CH$_2$), 36.34(CH$_2$), 27.93(CH$_2$), 25.82(CH$_3$), 25.44(CH$_2$), 18.21CH$_3$)

HPLC: The same conditions for Compound 11.

Elution time: 3.2 min.

EXAMPLE 9

Compound 1 (64 mg) was dissolved in methanol (10 ml) followed by addition of palladium black (20 mg) and the mixture was stirred under a hydrogen atmosphere at room temperature for 4 hours. The reaction mixture was then filtered and the filtrate was concentrated to dryness. The residue was purified by preparation HPLC [stationary phase YMC-Pack D-ODS-5; mobile phase 33% acetonitrile-0.05M sodium phosphate (pH 3)] to give fractions containing 7 and 13, respectively. Each of these fractions was concentrated, adjusted to pH 8.5 and extracted with ethyl acetate. The organic layer was washed with water, dehydrated over anhydrous sodium sulfate and concentrated to dryness to recover Compound 7 (15 mg) and Compound 13 (25 mg).

Compound 13

UV: Absorption maxima in methanol: 264 nm ($\epsilon$21,000), 304 nm ($\epsilon$1,900, shoulder)

$^1$H NMR spectrum (300 MHz, CDCl$_3$, $\delta$ ppm): 7.75(2H, d, J=8.8 Hz), 6.78(2H, d, J=8.8 Hz), 6.02(1H, d, J=1.3 Hz), 3.95 (2H, t, J=6.7 Hz), 3.25–3.35 (3H, m), 3.03 (1H, dd, J=1.5, 13.0 Hz), 2.95 (1H, dd, J=1.3, 13.7 Hz), 2.77 (1H, m), 2.20 (3H, s), 1.90–2.24 (5H, m), 1.60–1.90 (6H, m), 1.49 (1H, dd, J=5.4, 14.0 Hz), 0.95 (6H, d, J=6.6 Hz)

EXAMPLE 10

Compound 2 (80 mg) was dissolved in methanol (10 ml) followed by addition of palladium black (30 mg) and the mixture was stirred under a hydrogen atmosphere at room temperature for 4 hours. The reaction mixture was then filtered and the filtrate was concentrated to dryness. The residue was subjected to preparative HPLC [stationary phase YMC-Pack D-ODS-5; mobile phase 30% acetonitrile-0.05M sodium phosphate (pH 3)]. The eluate was treated in the same manner as in Example 9 to provide Compound 8 (33 mg) and Compound 14 (21 mg).

Compound 14

UV: Absorption maxima in methanol: 263 nm ($\epsilon$22,700), 303 nm ($\epsilon$1,600, shoulder)

$^1$H NMR spectrum (300 MHz, CDCl$_3$, $\delta$ ppm): 7.67 (2H, d, J=8.8 Hz), 6.78 (2H, d, J=8.8 Hz), 6.05 (1H, d, J=1.2 Hz), 4.53 (1H, dd, J=6.5, 12.1 Hz), 3.95 (2H, t, J=6.7 Hz), 3.43 (1H, dd, J=3.4, 12.1 Hz), 3.30 (1H, m), 3.28 (1H, d, J=13.7 Hz), 3.10 (1H, dd, J=1.6, 12.1 Hz), 2.94 (1H, dd, J=1.2, 13.7 Hz), 2.61 (1H, dd, J=4.0, 6.5, 13.0 Hz), 2.26 (1H, m), 2.18 (3H, s), 2.04–2.16 (2H, m), 1.70–1.90 (3H, m), 1.60–1.70 (2H, m), 0.95 (6H, d, J=6.6 Hz)

EXAMPLE 11

Compound 2 (23 mg) was dissolved in ethanol (0.5 ml) followed by addition of methyl iodide (25 $\mu$l) and the mixture was refluxed for 1 hour. After cooling, ether was added and the resulting precipitate was recovered by filtration. To the powder thus obtained was added water (5 ml) and the insoluble matter was filtered off. The filtrate was concentrated and freeze-dried to provide Compound 15 (24 mg).

UV: Absorption maxima in H$_2$O: 266 nm ($\epsilon$22,900), 303 nm ($\epsilon$1,700, shoulder)

Elemental analysis (for $C_{25}H_{35}N_2O_3I \cdot H_2O$) Calcd.: C, 53.96; H, 6.70; N, 5.03 Found: C, 54.20; H, 6.70; N, 4.86

$^1$H NMR spectrum (300 MHz, D$_2$O, $\delta$ ppm): 7.85 (2H, d, J=8.7 Hz), 6.93 (2H, d, J=8.7 Hz), 6.51 (1H, s), 5.43 (1H, t, J=7.0 Hz), 4.63 (1H, dd, J=7.0, 13.0 Hz), 4.50 (2H, d, J=7.0 Hz), 4.06–4.20 (2H, m), 3.97 (1H, d, J=15.0 Hz), 3.78 (1H, d, J=14.0 Hz), 3.64 (1H, d, J=14.0 Hz), 3.31 (3H, s), 3.17 (3H, s), 2.63 (1H, m), 2.45 (1H, d, J=16.0 Hz), 2.28 (1H, dd, J=6.0, 16.0 Hz), 1.74–2.22 (5H, m), 1.74 (3H, s), 1.67 (3H, s)

EXAMPLE 12

Compound 6 (100 mg) was dissolved in pyridine (1 ml) followed by addition of acetic anhydride (1 ml) and the mixture was allowed to stand at room temperature for 15 hours. The reaction mixture was then concentrated, diluted with water, adjusted to pH 8.5 and extracted with ethyl acetate. The organic layer was washed with a saturated aqueous solution of sodium chloride, dehydrated over anhydrous sodium sulfate and concentrated to dryness. The residue was purified by silica gel (6 g) column chromatography [solvent system: chloroform-methanol=98:2~96.4)] to provide Compound 16 (79 mg).

Specific rotation: +122.5° (D line, c 0.45, methanol, 25° C.)

UV: Absorption maxima in methanol: 265 nm ($\epsilon$22,600), 303 nm ($\epsilon$2,000, shoulder)

Elemental analysis (for $C_{26}H_{34}N_2O_4 \cdot \frac{1}{2}H_2O$) Calcd.: C, 69.77; H, 7.88; N, 6.26 Found: C, 69.2; H, 7.87; N, 6.16

$^{13}$C NMR spectrum (75 MHz, CDCl$_3$, $\delta$ ppm): 204.68(Q), 169.47(Q), 158.27(Q), 139.81(Q), 138.00(Q), 130.67(CH×2), 127.79(Q), 123.96(CH), 119.73(CH), 114.48(CH×2), 73.91(CH), 65.61(Q), 54.70(CH$_2$), 60.88(CH), 58.22(CH$_2$), 54. 94(CH$_2$), 43.60(CH$_2$), 41.96CH$_3$), 37.39 (CH$_2$), 35. 27(CH$_2$), 32.62(CH$_2$), 25.80(CH$_3$), 20.77(CH$_3$), 18.19(CH$_3$)

EXAMPLE 13

A 200 ml creased Erlenmyer's flask containing 30 ml of a fermentation medium (pH 6.7) composed of 5% glycerol, 2.5% sucrose, 0.5% peptone, 0.2% yeast extract, 0.3% ammonium sulfate and 0.5% calcium carbonate was inoculated with a preculture (inoculum size 1 ml) of *Penicillium thomii* RA-89 prepared in the same manner as Example 1. Separately, a solution of TAN-1251A in dimethyl sulfoxide was diluted 10-fold with methanol, and 0.3 ml of the dilution was added concurrently with inoculation. The flask was incubated on a rotary shaker at 24° C. for 72 hours. The assay of TAN-1251A and B was carried out by HPLC under the Conditions set forth under the heading of Physicochemical Properties. The results are shown in Table 4. It is apparent that approximately 60% of TAN-1251A added was hydroxylated to TAN-1251B.

TABLE 4

| Cultural conditions | Incubation time | TAN-1251A μg/ml | TAN-1251B μg/ml |
|---|---|---|---|
| Without TAN-1251A | 0 | 0 | 0 |
|  | 24 | 0 | 0 |
|  | 48 | 0.3 | 1.8 |
|  | 72 | 0.6 | 2.7 |
| With TAN-1251A | 0 | 28.0 | 0 |
|  | 24 | 25.4 | 0.2 |
|  | 48 | 16.2 | 10.4 |
|  | 72 | 11.1 | 17.2 |

We claim:

1. A compound of the formula wherein R$^1$ is hydrogen or a substituted or unsubstituted alkyl, alkenyl, or alkynyl group; R$^2$ is oxo or hydrogen and hydroxy, which may be acylated; R$^3$ is hydrogen or hydroxy which may be acylated; at least one of the dotted lines represents a single bond, or a salt thereof.

2. A compound according to claim 1, wherein R$^1$ is an alkenyl group which may be substituted.

3. A compound according to claim 1, wherein R$^2$ is oxo.

4. A compound according to claim 1, wherein R$^3$ is hydrogen.

5. A compound according to claim 1, wherein R$^3$ is hydroxy.

6. A compound according to claim 2, wherein the alkenyl group is 3-methyl-2-butenyl.

7. A compound according to claim 1, wherein R$^1$ is 3-methyl-2-butenyl, R$^2$ is oxo, R$^3$ is hydrogen, the dotted line on the right-hand side represents a single bond and the one of the left-hand side represents a double bond.

8. A compound according to claim 1, wherein R$^1$ is 3-methyl-2-butenyl, R$^2$ is oxo, R$^3$ is hydroxy, the dotted line on the right-hand side represents a single bond and the one on the left-hand side represents a double bond.

9. A compound according to claim 1, wherein R$^1$ is 3-methyl-2-butenyl, R$^2$ is oxo, R$^3$ is hydrogen, the dotted line on the right-hand side represents a double bond and the one on the left-hand side represents a single bond.

10. A compound according to claim 1, wherein R$^1$ is 3-methyl-2-butenyl, R$^2$ is oxo, R$^3$ is hydrogen, and both dotted lines represent single bonds.

11. A method of producing a compound of the formula wherein R$^{3'}$ is hydrogen or a hydroxy; at least one of the dotted lines represents single bond; provided that where R$^{3'}$ is hydroxy, the dotted line on the right-hand side represents a single bond and the one of the left hand side represents a double bond, or a salt thereof, comprising culturing [a strain of microorganism belonging to the genus *Penicillium thomii* RA-89 or a mutant thereof capable of producing at least one compound having the above formula in a culture medium and recovering the compound from the resulting culture broth.

12. An antispasmodic and antiulcer composition comprising a therapeutically effective amount of a compound of the formula wherein R$^1$ is hydrogen of a substituted or alkyl, alkenyl, or alkynyl hydrogen group R$^2$ is oxo or hydrogen and hydroxy which may be acylated; R$^3$ is hydrogen or hydroxy which may be acylated; at least one of the dotted lines represents a single bond, or a pharmacologically acceptable salt thereof, and in combination with pharmacologically acceptable carriers.

* * * * *